(12) United States Patent
Szivacz et al.

(10) Patent No.: US 10,369,514 B2
(45) Date of Patent: Aug. 6, 2019

(54) DEVICE AND METHOD FOR SEPARATING A GAS MIXTURE

(71) Applicant: AXIOM ANGEWANDTE PROZESSTECHNIK GES.M.B.H., Ebreichsdorf (AT)

(72) Inventors: Johannes Szivacz, Ebreichsdorf (AT); Johannes Wintersperger, Ebreichsdorf (AT)

(73) Assignee: AXIOM ANGEWANDTE PROZESSTECHNIK GES.M.B.H., Ebreichsdorf (AT)

( * ) Notice: Subject to any disclaimer, the term of this patent is extended or adjusted under 35 U.S.C. 154(b) by 64 days.

(21) Appl. No.: 15/527,855

(22) PCT Filed: Sep. 9, 2016

(86) PCT No.: PCT/EP2016/071261
§ 371 (c)(1),
(2) Date: May 18, 2017

(87) PCT Pub. No.: WO2017/042310
PCT Pub. Date: Mar. 16, 2017

(65) Prior Publication Data
US 2018/0333674 A1    Nov. 22, 2018

(30) Foreign Application Priority Data

Sep. 10, 2015 (EP) .................................... 15184639

(51) Int. Cl.
*B01D 53/22* (2006.01)
*B01D 53/30* (2006.01)
(Continued)

(52) U.S. Cl.
CPC ............. *B01D 53/22* (2013.01); *B01D 53/30* (2013.01); *C07C 7/144* (2013.01); *C10L 3/104* (2013.01);
(Continued)

(58) Field of Classification Search
None
See application file for complete search history.

(56) References Cited

U.S. PATENT DOCUMENTS

| 4,130,403 A | 12/1978 | Cooley et al. .................... 95/49 |
| 2012/0111052 A1* | 5/2012 | Szivacz ................ B01D 53/226 62/619 |

(Continued)

FOREIGN PATENT DOCUMENTS

| EP | 2679297 | 1/2014 |
| EP | 2762220 | 8/2014 |

(Continued)

OTHER PUBLICATIONS

Agrawal et al., "Gas Separation Membrane Cascades II. Two-compressor Cascades," *Journal of Membrane Science*, 1996; 112: 129-146.

*Primary Examiner* — Tam M Nguyen
(74) *Attorney, Agent, or Firm* — Norton Rose Fulbright US LLP

(57) ABSTRACT

The invention relates to a device for separating a gas mixture into a product gas and an offgas by gas permeation, having a membrane unit (I) and a compressor (3) that is connected upstream of the membrane unit (I) and is preferably adjustable in terms of rotational speed, which membrane unit (I) has a gas inlet (I a), an outlet (I b) for retentate or product gas, and an outlet (I c) for permeate or offgas, wherein the membrane unit (I) has at least one other permeate outlet (1c') that is downstream of the gas inlet (1a), and the permeate outlet (1c') of the membrane unit (I) is connected by lines on (Continued)

the suction side to the compressor (3) or to the gas supply leading into the compressor, and wherein a pressure-regulating device (2) is provided at or downstream of the retentate outlet (Ib), and use is made of a gas mixture, consisting primarily of CH4/CO2 and having a methane concentration of not greater than 30% by volume; and to the use of such a device and to a corresponding method.

11 Claims, 5 Drawing Sheets

(51) Int. Cl.
  *C10L 3/10* (2006.01)
  *C07C 7/144* (2006.01)
(52) U.S. Cl.
  CPC .. *B01D 2256/245* (2013.01); *B01D 2257/504* (2013.01); *B01D 2258/05* (2013.01); *C10L 2290/548* (2013.01); *Y02C 10/10* (2013.01)

(56) References Cited

U.S. PATENT DOCUMENTS

| 2016/0229771 A1* | 8/2016 | Paget | B01D 53/226 |
| 2017/0320736 A1* | 11/2017 | Voss | B01D 53/226 |
| 2018/0112142 A1* | 4/2018 | Foody | B01D 53/047 |
| 2018/0223205 A1* | 8/2018 | Mitariten | B01D 53/229 |

FOREIGN PATENT DOCUMENTS

| FR | 2917305 | 12/2008 |
| WO | WO 2010/141963 | 12/2010 |

\* cited by examiner

Fig. 5

Membrane unit operated in counter-current flow

| | Feed | | | Off gas | | | Product | | | |
|---|---|---|---|---|---|---|---|---|---|---|
| | % | Nm³/h | kWh/Nm³ RG | % | Nm³/h | % | Nm³/h | kWh/Nm³ RG | Recovery % | Selectivity CO₂/CH₄ |
| CH₄ | 16.00 | 0.4960 | 0.1107 | 1.19 | 0.0274 | 59.21 | 0.4689 | 0.4335 | 94.48 | 55.00 |
| CO₂ | 84.00 | 2.6040 | | 98.81 | 2.2606 | 40.79 | 0.3231 | | | |
| Total | | 3.1000 | | | 2.3080 | | 0.7920 | | | |

Membrane unit operated in co-current flow

| | Feed | | | Off gas | | | Product | | | |
|---|---|---|---|---|---|---|---|---|---|---|
| | % | Nm³/h | kWh/Nm³ RG | % | Nm³/h | % | Nm³/h | kWh/Nm³ RG | Recovery % | Selectivity CO₂/CH₄ |
| CH₄ | 16.00 | 0.4960 | 0.1107 | 1.19 | 0.0273 | 58.52 | 0.4682 | 0.4287 | 94.44 | 55.00 |
| CO₂ | 84.00 | 2.6040 | | 98.81 | 2.2727 | 41.48 | 0.3318 | | | |
| Total | | 3.1000 | | | 2.3000 | | 0.8000 | | | |

Membrane operated according to the invention (50% of surface in counter-current flow - 50% of surface in co-current flow)

| | Feed | | | Off gas | | | Product | | | |
|---|---|---|---|---|---|---|---|---|---|---|
| | % | Nm³/h | kWh/Nm³ RG | % | Nm³/h | % | Nm³/h | kWh/Nm³ RG | Recovery % | Selectivity CO₂/CH₄ |
| CH₄ | 16.00 | 0.4960 | 0.1586 | 0.39 | 0.0061 | 31.92 | 0.4900 | 0.3205 | 98.78 | 55.00 |
| CO₂ | 84.00 | 2.6040 | | 99.61 | 1.5589 | 68.08 | 1.0450 | | | |
| Total | | 3.1000 | | | 1.5650 | | 1.5350 | | | |

| Operation in counter- / co-current flow | | | |
|---|---|---|---|
| kWh/Nm3 RG | Membrane surface in co-current flow | Recovery | |
| 0.1107 | 0 | 94.48 | progressive operation possible |
| 0.1155 | 0.1 | 95.68 | |
| 0.123 | 0.2 | 96.74 | |
| 0.1333 | 0.3 | 97.61 | |
| 0.1454 | 0.4 | 98.28 | |
| 0.1586 | 0.5 | 98.78 | |

DEVICE AND METHOD FOR SEPARATING A GAS MIXTURE

CROSS-REFERENCE TO RELATED APPLICATIONS

This application is a national phase application under 35 U.S.C. § 371 of International Application No. PCT/EP2016/071261 filed 9 Sep. 2016, which claims priority to European Patent Application No. 15184639.1 filed 10 Sep. 2015. The entire contents of each of the above-referenced disclosures is specifically incorporated by reference herein without disclaimer.

BACKGROUND

1. Field of the Invention

The present invention relates to a device and a method for separating a mixture of gases into product gas and off gas by means of gas permeation.

In gas permeation membrane units, the separation of product gas and off gas is conducted by means of permeation, wherein, for example, a product gas-enriched retentate and an off gas-enriched permeate can be obtained. The product gas concentrations in the retentate and the off gas concentrations in the permeate are, among other factors, dependent on the process parameters employed in each case; in general, an increased product gas quality will always require an increased use of energy (due to higher pressures, lower yields with respect to the feed gas used, and the like). Improved methods for increasing the product gas yield or for a more efficient utilization of energy in the course of such a method are thus desirable. Furthermore, it is desirable to keep investment costs for setting up a gas permeation plant as low as possible.

2. Description of Related Art

According to the state of the art, devices for separating a mixture of gases into product gas and off gas by means of gas permeation are designed such that the pressurized feed gas is separated into retentate and permeate in a membrane unit, wherein, for example, the retentate contains the product gas and the permeate contains the off gas. Disadvantages to this one-step solution are low product gas quality and low product gas yield, which entails an increased energy demand. Furthermore, an economical utilization of this device is only possible with the use of highly selective membranes.

Improved devices for separating a mixture of gases into product gas and off gas by means of gas permeation are designed such that the permeate of a first membrane unit is used in pressurized form as a feed gas for a second membrane unit, wherein the retentate flows of both membrane units contain the product gas and the permeate flow of the second membrane unit contains the off gas. Optionally, a compressor may be arranged upstream of the plant, unless the feed gas is present in a pressurized form. The advantage of this device is an improved product gas yield. Disadvantages to this solution are the still low product gas quality and an increased energy demand due to the required compaction of the gas for the second membrane unit. Furthermore, an economical utilization of this device is only possible with the use of highly selective membranes.

Furthermore, devices are known in which the retentate of a first membrane unit is used as a feed gas for a second membrane unit, the permeate of the second membrane unit is admixed to the pressurized feed gas of the first membrane unit, the retentate of the second membrane unit is withdrawn as a product gas and the permeate of the first membrane unit is withdrawn as an off gas. As in this case the permeate of the second membrane unit is circulated, in a manner of speaking, the dimensions of the plant and all required parts thereof (compressors, conduits, membrane units, cold separators, precision sulfur separators etc.) must be enlarged corresponding to the volume flow of the circulated permeate of the first membrane unit. Assuming a feed gas volume flow of 100 m$^3$/h and the admixture of 80 m$^3$/h of permeate of the second membrane unit to said feed gas will yield a total volume flow of 180 m$^3$/h upstream of the compressor, according to which the plant is to be dimensioned. Advantageous to this method is the fact that a higher product gas yield can be obtained and that less selective membranes are used due to the two-step implementation; disadvantageous is the required oversized (by a factor of 1.2 to 2.5) dimensioning of the plant and the increased energy demand owing to recirculation.

Document U.S. Pat. No. 4,130,403 A (D1) discloses the back coupling of the retentate outlet of a membrane unit to the gas supply of a further membrane unit, which has only one single membrane unit arranged upstream thereof.

Agrawal R. et al. (Journal of Membrane Science, Elsevier Scientific Publ. Company, Vol. 112, No. 2) relates to cascading arrangements with two compressors. FIG. 6 shows back couplings to the gas inlet of the respective first membrane unit.

Document FR 2 917 305 A1 (D3) discloses a matrix arrangement of a plurality of membrane units.

Known from document WO 2010/141963 A1 is a device for separating a mixture of gases into product gas and off gas by means of gas permeation, said device having at least two membrane units (1) and (2) as well as a compressor (3) arranged upstream of the first membrane unit (1), wherein the membrane units (1) and (2) each have a gas inlet (1a, 2a), a retentate outlet (1b, 2b) and a permeate outlet (1c, 2c), wherein the retentate outlet (1b) of the first membrane unit (1) is connected via conduits to the gas inlet (2a) of the second membrane unit (2), the permeate outlet (2c) of the second membrane unit (2) is connected via conduits to the compressor (3) or the gas supply leading into the compressor on the suction side thereof, and the compressor (3) is connected via conduits to the gas inlet (1a) of the first membrane unit (1), product gas is obtained via the retentate outlet (2b) and off gas is obtained via the permeate outlet (1c).

According to WO 2010/141963 A1 it is provided in such a device that the permeate outlet (4c) of an upstream membrane unit (4) is connected via conduits to the gas supply of the compressor (3), wherein the membrane unit (4) has at least one further upstream membrane unit (5), which is formed by connecting the retentate outlet (5b) of said further membrane unit (5) to the gas inlet (4a) of the membrane unit (4) via conduits, and wherein additional product gas is obtained via the retentate outlet (4b) and additional off gas is obtained via the permeate outlet (5c).

All these devices have in common that the individual membrane units are always operated in counter-current flow.

Known from document WO 2010/141963 A1 are membrane units having a gas inlet, a retentate outlet and two permeate outlets, wherein the permeate spaces of such membrane units may be separated by a wall in the area located between both permeate outlets. Such membrane units are supposed to allow for an increased product gas yield.

SUMMARY OF THE INVENTION

It is thus the object of the present invention to provide a device and a method for separating a mixture of gases into product gas and off gas by means of gas permeation which allows for a minimum possible concentration of product gas in the off gas, adjustable by controlling the device, as well as for a more efficient utilization of energy.

To this end, the present invention provides a device for separating a mixture of gases into product gas and off gas by means of gas permeation, said device having a membrane unit (1) and a preferably rotational speed-adjustable compressor (3) arranged upstream of the membrane unit (1), which membrane unit (1) has a gas inlet (1a), a retentate or product gas outlet (1b) and a permeate or off gas outlet (1c), wherein the membrane unit (1) has at least one further permeate outlet (1c') arranged downstream of the gas inlet (1a) and the permeate outlet (1c') of the membrane unit (1) is connected via conduits to the compressor (3) or the gas supply leading into the compressor (3) on the suction side thereof. According to the present invention, a pressure control unit (2) is provided at or downstream of the retentate outlet (1b) and a mixture of gases mainly consisting of $CH_4/CO_2$ and having a methane concentration of not more than 30% by volume is used. This combination of a pressure control unit and a specific mixture of gases (wherein, for the purposes of the present invention, "mainly" refers to a proportion present in the mixture of gases of more than 50% by volume, preferably more than 55% by volume, 60% by volume, 65% by volume, 70% by volume, 75% by volume, 80% by volume, 85% by volume, particularly preferred more than 90% by volume or 95% by volume), which limits the methane concentration in the feed gas and at the same time provides a resistance in the retentate space by means of the retentate pressure control unit and may, for example, be represented by a valve or control valve, the suction side of a preferably rotational speed-adjustable compressor or (also preferably rotational speed-adjustable) compressor or a supply leading to a stage of a preferably rotational speed-adjustable multi-stage compressor, allows for closing the pressure control unit in an adjustable manner corresponding to the respective presets or for providing a resistance through the rotational speed of the compressor or for adjusting the rotational speed of the compressor by means of regulating or controlling. In this context, closing of the control valve (2) does not necessarily entail a pressure increase in the retentate space; for example, the closing of the control valve (2) may entail a decrease in rotational speed of the compressor (3), which will eventually leave the pressure in the retentate space constant instead of increasing it. Here, the only prerequisite is the provision of a resistance on the retentate side of the membrane unit according to the present invention for the mixture of gases present therein. In this manner, the membrane unit can be operated in co-current flow in the area of the second permeate outlet (1c') located downstream of the gas inlet, in an at least partially controlled manner, while the membrane unit is mainly operated in the usually applied counter-current flow in the area of the first permeate outlet. In this context, "at least partially" or "mainly" are not supposed to mean that a co-current flow and a counter-current flow prevail at both permeate outlets simultaneously (which is technically impossible), but rather that the permeate exiting at the respective permeate outlet originates from a membrane area which, depending on the selected conditions, on the permeate side actually has been operated in either co-current or counter-current flow with respect to the flow direction on the retentate side. This results in surprising and significant improvements in the operation of the device according to the present invention, mainly with respect to a decrease of the product gas concentration in the off gas, but also with respect to an increase in the amount of product gas. Thus, according to the present invention, the separation of a mixture of gases mainly consisting of $CH_4/CO_2$, for example lean gas, mine gas or bio gas, into $CH_4$ as a product gas and mainly $CO_2$ as an off gas by means of the device according to the present invention can be conducted so as to achieve a surprisingly high recovery of more than 98% of $CH_4$ in the product gas, preferably up to 99.8%, as long as the methane concentration in the feed gas does not exceed 30% by volume, as is provided according to the present invention. Of course, it is also possible to operate the pressure control unit in an automated manner, for example if sensors are provided in suitable locations of the device according to the present invention, by opening or closing the pressure control unit with the aid of a control unit in order to adhere to a predefined limit value which is measured in one or more locations inside or outside the device according to the present invention. The limit value may, for example, represent the methane concentration in the off gas, in which case the sensor may be a gas sensor provided at or near the permeate outlet (1c). In Germany, for example, the release of methane (product gas or retentate in the separation of bio gas by means of gas permeation), in terms of the maximum emittable amount of methane in the off gas, is limited to 0.2% by volume of the total methane mass produced in the bio gas process, wherein, for example, the adherence to this limit value by means of the device according to the present invention may also be provided in an automated manner with the aid of a control unit. By connecting the permeate outlet (1c') of the membrane unit (1) to compressor (3) or the gas supply leading to the compressor via conduits on the suction side thereof, it is provided that the permeate can be supplied to the feed gas before or during its pressurization. Should said supply require an increased pressure level, said increased pressure level can be achieved by means of additionally provided compressors (which will not be explicitly referred to in the following). In an ideal case, an off gas ($CO_2$) exiting the device according to the present invention via the permeate outlet (1c) can be directly emitted or reused without any further purification with respect to its methane content.

According to a preferred embodiment of the present invention, a preferably rotational speed-adjustable compressor (4) and/or a pressure control unit (5) is/are provided at or downstream of the first permeate outlet (1c). Providing a pressure control unit, for example a valve or control valve, allows for generating a back pressure upon a decrease of the flow rate through the valve located in the permeate space of the device according to the present invention, thereby increasing the area of the separation membrane which is operated in co-current flow. If, on the other hand, a preferably rotational speed-adjustable compressor is operated at or downstream of the first permeate outlet (1c), the withdrawal of off gas from the first permeate outlet (1c) is increased and the area of the separation membrane which is operated in co-current flow is reduced. With the provision of both a pressure control unit and a preferably rotational speed-adjustable compressor, the device according to the present invention can thus be controlled in any direction.

It is also advantageous to provide a pressure control unit (6) in the conduit leading from the permeate outlet (1c') of the membrane unit (1) to the compressor (3) or the gas supply leading to the compressor on the suction side thereof. Similar as in case of the above-described preferred embodiment, the provision of a pressure control unit in the conduit leading from the permeate outlet (1c') of the membrane unit (1) to the compressor (3) or the gas supply leading to the compressor on the suction side thereof allows for increasing the back pressure into the permeate space of the device according to the present invention (when the pressure control unit, for example a valve or control valve, reduces the gas flow rate), which leads to a reduction of the area of the separation membrane which is operated in co-current flow. If, on the other hand, the pressure control unit is opened, the suction capacity of the compressor (3) will yield a pressure loss in the permeate space, at least in the area of the permeate outlet (1c'), which in turn increases the area of the separation membrane which is operated in co-current flow. However, the scope of the present invention also encompasses an embodiment in which the conduit exiting the permeate outlet (1c') of the membrane unit (1) leads to a compressor or to the gas supply leading to the compressor of a parallel membrane unit on the suction side thereof. Preferably, said conduit is also equipped with the pressure control unit (6) which is controlled or regulated in a manner dependent on the concentration of product gas in the off gas.

According to the present invention it is also provided that the rotational speed-adjustable compressor (3) and the pressure control unit (2) are connected to a control unit (7). The provision of, for example, a gas sensor in the area of the permeate outlet (1c), which gas sensor is, for example, capable of directly or indirectly measuring the product gas concentration in the off gas, allows for an operation of the device according to the present invention such that a predefined product gas proportion in the off gas will not be exceeded, as already mentioned above.

Another preferred embodiment of the present invention is characterized in that the preferably rotational speed-adjustable compressor (4) and/or the pressure control unit (5) is/are connected to a/the control unit (7). The provision of, for example, a gas sensor in the area of the permeate outlet (1c), which gas sensor is, for example, capable of directly or indirectly measuring the product gas concentration in the off gas, allows for an operation of the device according to the present invention such that a predefined product gas proportion in the off gas will not be exceeded, as already mentioned above.

In this context, it is also advantageous if the pressure control unit (6) is connected to a/the control unit (7). The provision of, for example, a gas sensor in the area of the permeate outlet (1c), which gas sensor is, for example, capable of directly or indirectly measuring the product gas concentration in the off gas, allows for an operation of the device according to the present invention such that a predefined product gas proportion in the off gas will not be exceeded, as already mentioned above.

According to another aspect of the present invention, said device is employed for separating a mixture of gases mainly consisting of $CH_4/CO_2$ into $CH_4$ as a product gas and mainly $CO_2$ as an off gas. Examples of such mixtures of gases are lean gas, mine gas, bio gas and the like.

Yet another aspect of the present invention relates to a method for separating a mixture of gases into product gas and off gas by means of gas permeation, characterized in that the permeate of a membrane unit (1) is recovered partially in co-current flow and partially in counter-current flow, wherein the permeate recovered in co-current flow is pressurized and recirculated to the membrane unit (1) as a feed gas, the permeate recovered in counter-current flow is withdrawn as an off gas, and furthermore the retentate of the membrane unit (1) is withdrawn as a product gas, wherein the withdrawal of the permeate recovered in co-current flow is controlled or regulated in a manner dependent on the concentration of product gas in the off gas. In this case, the withdrawal of the permeate recovered in co-current flow is conducted via said pressurization, whereby the permeate of the membrane unit is recirculated as a feed gas.

Preferably, it is provided that the pressure of the retentate in the membrane unit (1) is increased. As already explained, the provision of a resistance (according to the above disclosure with respect to the resistance (2)) will, for example, lead to an increase of the pressure of the retentate present in the membrane unit, which in turn results in an increase of the amount of permeate recovered in co-current flow.

BRIEF DESCRIPTION OF THE DRAWINGS

The present invention will now be explained in more detail with reference to the accompanying drawings, in which:

FIG. 5 shows a comparison of the respective values obtained when operating the same membrane unit in counter-current flow, in co-current flow and according to the present invention (with a partial operation in co-current flow);

DETAILED DESCRIPTION

Figure 1:
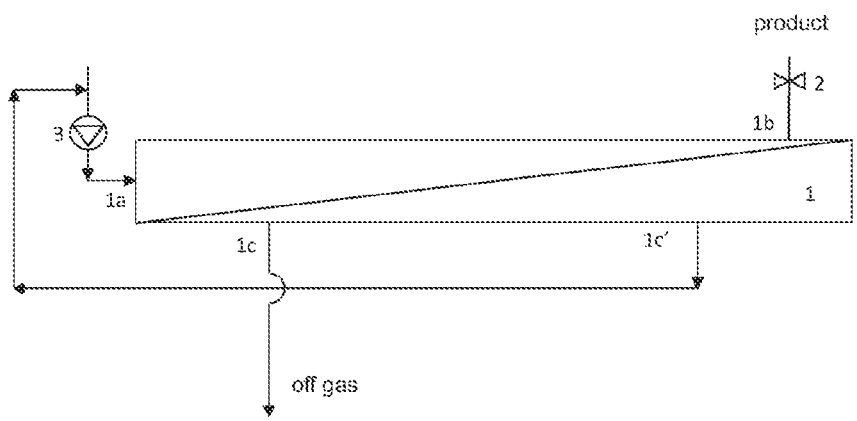
FIG. 1 shows a block diagram of a device according to the present invention having a membrane unit (1), a pressure control unit (2) and a compressor (3) arranged upstream of the membrane unit (1)

The membrane unit according to FIG. 1 has a gas inlet (1a), a retentate outlet (1b) and an additional permeate outlet (1c'). In the membrane unit (1), the off gas present in the area operated in counter-current flow is discharged via the permeate outlet (1c) and the permeate suctioned off via the permeate outlet (1c') by the compressor (3) in the area operated in co-current flow is recirculated as a feed gas to the membrane unit (1) via the compressor (3). In this manner, the off gas separated via compressor (3), gas inlet (1a) and permeate outlet (1c') in the membrane unit (1) in the area operated in co-current flow is circulated. The product gas is discharged via the retentate outlet (1b), wherein the pressure control unit (2) arranged there serves to increase the pressure in the retentate space of the membrane unit (1), whereby the operation of the separation membrane according to the present invention in partial co-current flow is rendered controllable. With respect to FIG. 1—irrespective of where exactly the permeate outlets are located relative to one another (with the exception that the permeate outlet (1c') must be located downstream of the gas inlet (1a)), the following applies:

With respect to the permeate outlet (1c), a permeate originating from the left area (as viewed from outlet (1c)) of the permeate space is recovered in co-current flow as the flow direction of the retentate from the gas inlet (1a) to the retentate outlet (1b) corresponds to the flow direction from the left area of the permeate space to the permeate outlet (1c). On the other hand, a permeate originating from the right area (as viewed from outlet (1c)) of the permeate space is recovered in counter-current flow as the flow direction of the retentate from the gas inlet (1a) to the retentate outlet (1b) is opposite to the flow direction from the right area of the permeate space to the permeate outlet (1c).

This is similar with respect to the permeate outlet 1c', where a permeate originating from the left area (as viewed from the outlet (1c')) of the permeate space is also recovered in co-current flow as the flow direction of the retentate from the gas inlet (1a) to the retentate outlet (1b) corresponds to the flow direction from the left area of the permeate space to the permeate outlet (1c'). On the other hand, a permeate originating from the right area (as viewed from outlet (1c')) of the permeate space is recovered in counter-current flow as the flow direction of the retentate from the gas inlet (1a) to the retentate outlet (1b) is opposite to the flow direction from the right area of the permeate space to the permeate outlet (1c'). It is obvious that no permeate originating from areas of the membrane which have been operated exclusively in the co-current mode or exclusively in the counter-current mode, respectively, can be present at either of the permeate outlets.

Figure 2:
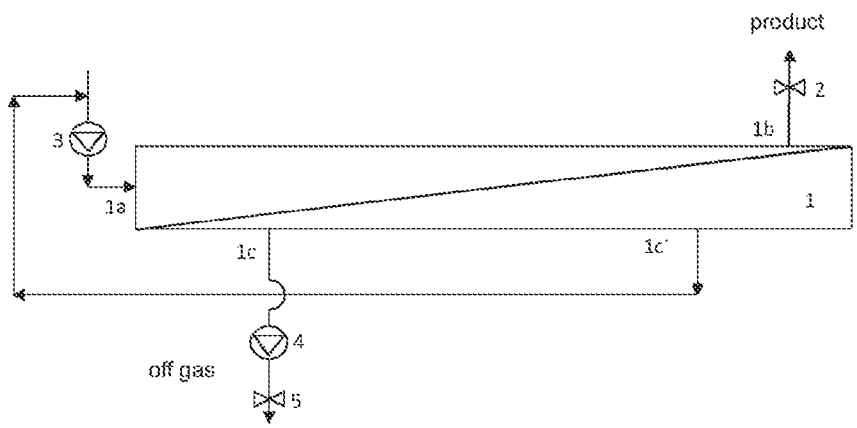
FIG. 2 shows a block diagram of the device according to FIG. 1 having an additional second pressure control unit (5) and an additional second compressor (4)

FIG. 2 shows the embodiment according to FIG. 1, wherein a second pressure control unit (5) and a second, preferably rotational speed-adjustable compressor (4) is provided in the conduit connected to the permeate outlet (1c). When the pressure control unit (5) is closed, off gas will back up into the retentate space of the membrane unit (1), which inevitably leads to an increased discharge of retentate through the retentate outlet (1c'), whereby the area of the separation membrane which is operated in co-current flow is increased. If, on the other hand, the pressure control unit (5) is fully opened and the preferably rotational speed-adjustable compressor (4) is started, an increased discharge of retentate through the retentate outlet (1c) is bound to occur, which in turn results in an increase in withdrawal of off gas from the first permeate outlet (1c) as well as to a decrease of the area of the separation membrane which is operated in co-current flow.

Figure 3:
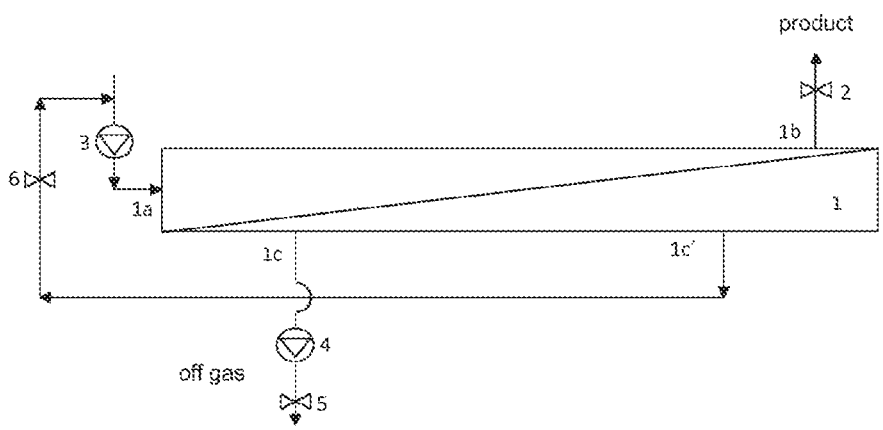
FIG. 3 shows a block diagram of the device according to FIG. 2 having an additional third pressure control unit (6)

FIG. 3 shows the embodiment according to FIG. 2, wherein a further pressure control unit (6) is provided in the conduit between the permeate outlet (1c') and the compressor (3) or the supply conduit leading to the compressor (3). This pressure control unit (6) allows for a reduction of the discharge of permeate from the permeate space of the membrane unit (1) via the permeate outlet (1c'), irrespective of the capacity of the compressor (3), whereby the pressure conditions in the permeate space near the permeate outlet (1c') are altered. Generating a back pressure leads to an increased push of retentate toward the retentate outlet (1c), whereby the area of the separation membrane which is operated in co-current flow is also reduced.

Figure 4:
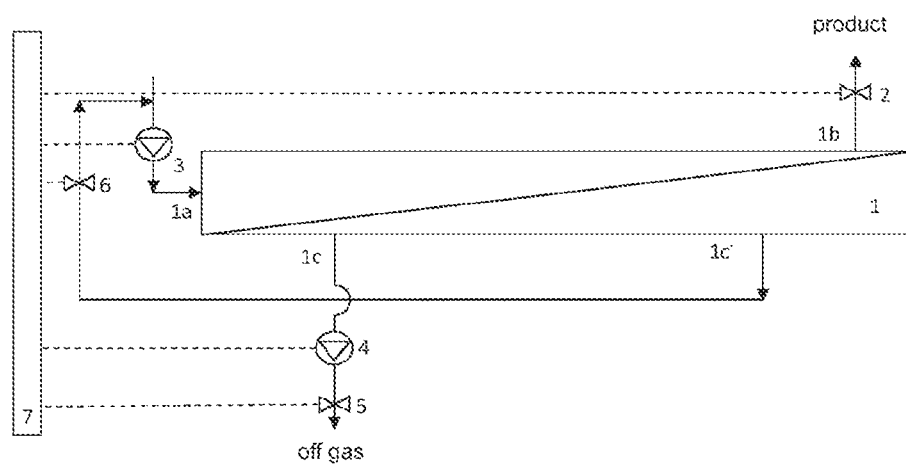
FIG. 4 shows a block diagram of the device according to FIG. 3 having an additional control unit (7)
Figure 6:
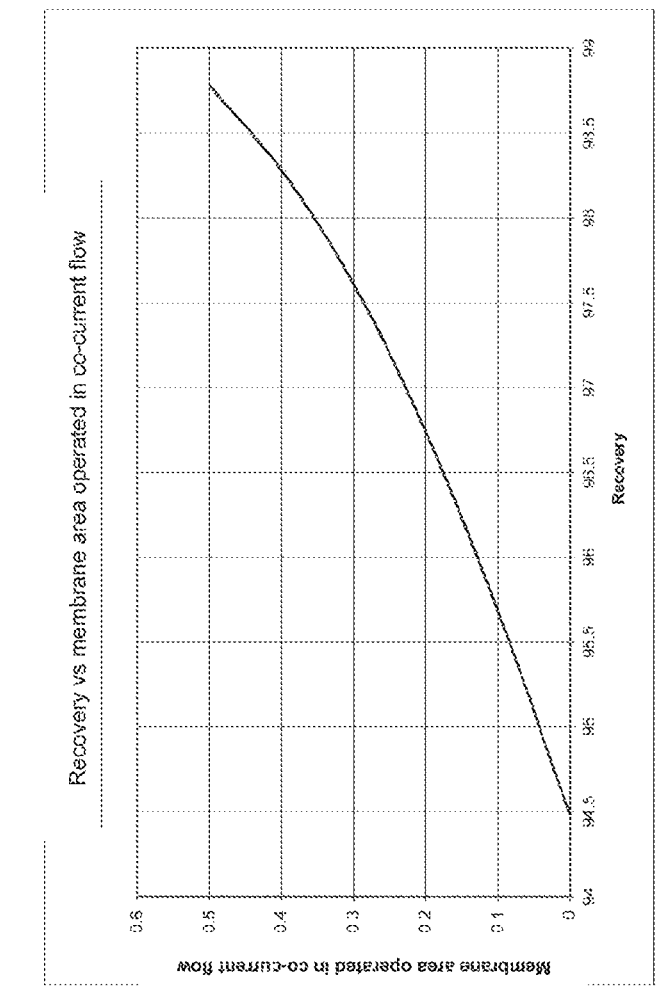
FIG. 6 shows the recovery results with a progressive alteration of the membrane area operated in co-current flow, using the same membrane unit as for the results shown in FIG. 5.

FIG. 4 shows the embodiment according to FIG. 3, wherein the pressure control units (2, 5, 6) and the compressor (3, 4) are connected to a control unit (7). In this context, it is explicitly noted that the present invention also provides a connection of the individual units (2, 3, 4, 5, 6) with the control unit. Sensors which are possibly required for the operation of the control unit, for example gas sensors, pressure sensors and/or flow rate sensors, are not shown in FIGS. 1 to 4. The control unit (7) is designed to be able to provide the independent opening and closing of the pressure control units (2, 5, 6) as well as the (also independent) adjustment of the rotational speed of the compressors (3, 4).

As is obvious from FIG. 5, the values for the operation of the membrane unit in counter-current flow and in co-current flow, respectively, differ only slightly; a significant increase of the recovery rate can only be observed when operating the membrane area partially in counter-current flow and partially in co-current flow. This is advantageous because the use of the membrane unit according to the present invention or the operation of the membrane unit according to the present invention with a methane concentration in the feed gas of not more than 30% by volume allows for a reduction of the methane proportion in the off gas to hitherto impossibly low values, which is particularly advantageous with respect to the efficiency of the separation of methane from the feed gas employed. It is understood that the device according to the present invention cannot only be used for separating methane from a methane-containing feed gas, but is also suitable for significantly increasing the recovery of product gas for any mixture of gases, as long as permeation membranes suitable for the respective mixture of gases are used.

Figure 7A:
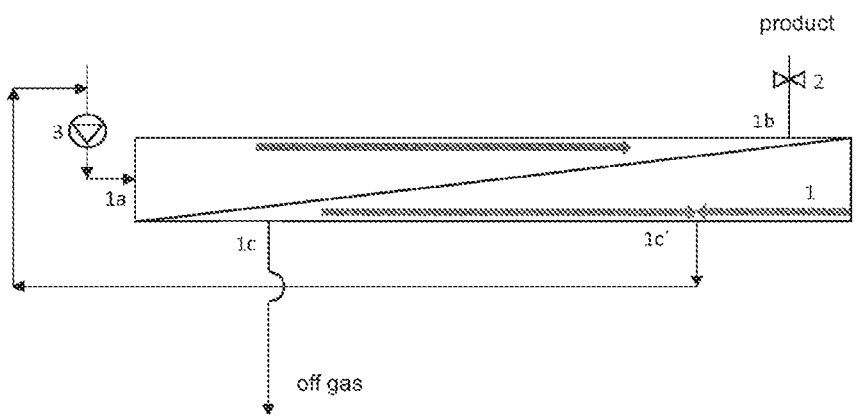
FIGS. 7a and 7b show an illustration of the terms "co-current" and "counter-current" and "at least partially" and "mainly", respectively, as used in the present invention.

As can easily be seen from FIG. 7a, with reference to FIG. 1, the greater proportion (i. e. more than half) of the permeate exiting or being suctioned off via the permeate outlet (1c') originates from the membrane areas operated in co-current flow.

Figure 7B:
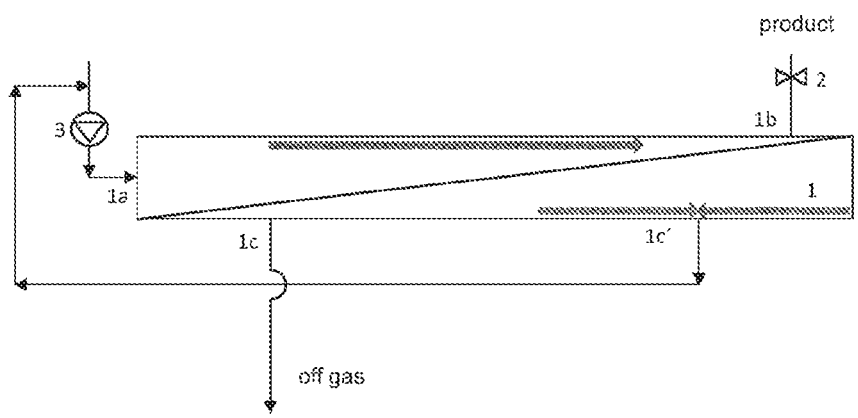

If now, based on the situation as depicted in FIG. 7a, the rotational speed of the compressor (3) is reduced, the composition of the permeate exiting or being suctioned off via the permeate outlet (1c') will also be altered and a smaller proportion of the permeate obtained will originate from the membrane areas operated in co-current flow (see FIG. 7b).

As already explained, the pressure control unit serves for providing a resistance on the retentate side of the membrane unit according to the present invention; without the pressure control unit (2) there would be no back pressure in the retentate space and a separation would thus be impossible. According to the present invention, pressure increases in the retentate space are mainly provided by increasing the rotational speed of the compressor (3), whereby the amount of feed gas supplied to the membrane unit is also altered.

Moreover, it is obvious to the person skilled in the art that at a separation membrane employed according to the present invention there will always be a concentration gradient of methane permeating the membrane; however, the permeate present in the permeate space is richer in methane in the right part of the membrane (near the retentate outlet (1b)) than in the left part of the membrane (near the feed gas inlet (1a)).

If a resistance is generated on the retentate side of the membrane unit according to the present invention (for example by further closing the control valve (2), whereby pressure is built up in the retentate space) and the permeate outlet (1c') of the membrane unit (1) is connected via conduits to the compressor (3) or the gas supply leading to the compressor on the suction side thereof, permeate is withdrawn via the permeate outlet (1c') and is re-admixed with the feed gas. In this case, the composition of the permeate withdrawn via the permeate outlet (1c') can be influenced by the selected rotational speed of the compressor (3). Increasing the rotational speed will increase the amount of permeate originating from areas of the membrane that are operated in co-current flow (FIG. 7a) while decreasing the rotational speed will result in a corresponding reduction of the amount of permeate originating from areas of the membrane that are operated in co-current flow (FIG. 7b).

As it is possible to keep the total amount of permeate permeating the membrane virtually constant (a pressure increase in the retentate space caused by increasing the rotational speed of the compressor (3) and the associated altered separation capacity of the membrane can be compensated by correspondingly opening the pressure control unit (2) and thus reducing the resistance), it is possible according to the present invention to regulate the composition of the off gas with respect to its methane content by means of the rotational speed of the compressor (3).

The inventive effect, whose occurrence is limited to methane concentrations in the feed gas of not more than 30% by volume, however, is thus not achieved via the pressure control unit (2) alone as the latter merely serves for providing a resistance in the retentate space of the membrane unit according to the present invention. Rather, the desired effect is achieved via the rotational speed of the compressor (3), optionally in combination with the pressure control unit (2).

The invention claimed is:

1. A device for separating a mixture of gases into product gas and off gas by gas permeation comprising:
   a speed-adjustable compressor;
   a membrane unit downstream of the speed-adjustable compressor, the membrane unit comprising a gas inlet, a retentate or product gas outlet, a first permeate gas outlet, and at least one further permeate outlet located downstream of the gas inlet that is connected via a conduit to the compressor or a gas supply leading to the compressor; and
   a pressure control unit at or downstream of the retentate outlet;
   wherein the device is adapted to separate a mixture of gases comprising $CH_4$ and $CO_2$ and a methane concentration of not more than 30% by volume.

2. The device of claim 1, wherein the speed-adjustable compressor is a rotational speed-adjustable compressor.

3. The device of claim 1, further comprising a pressure control unit in the conduit leading from the at least one further permeate outlet of the membrane unit to the compressor or a gas supply leading to the compressor.

4. The device of claim 1, wherein the speed-adjustable compressor and/or the pressure control unit is/are connected to a control unit.

5. The device of claim 4, wherein the speed-adjustable compressor and the pressure control unit are connected to the control unit.

6. The device of claim 4, wherein the pressure control unit is connected to the control unit.

7. The device of claim 1, comprising a second speed-adjustable compressor and/or a second pressure control unit at or downstream of the first permeate gas outlet.

8. The device of claim 7, comprising a second speed-adjustable compressor further defined as a rotational speed-adjustable compressor.

9. The device of claim 7, wherein the second speed-adjustable compressor and/or the second pressure control unit is/are connected to a control unit.

10. The device of claim 7, comprising a second speed-adjustable compressor and a second pressure control unit at or downstream of the first permeate gas outlet.

11. The device of claim 10, wherein the second speed-adjustable compressor and the second pressure control unit are connected to the control unit.

* * * * *